United States Patent [19]

Duhé et al.

[11] 4,259,318
[45] Mar. 31, 1981

[54] POISON IVY RELIEF COMPOSITION

[75] Inventors: Nanda V. Duhé, Cypress; Donald L. Hendrix, Bellaire, both of Tex.

[73] Assignee: University of Houston, Central Campus, Houston, Tex.

[21] Appl. No.: 882,899

[22] Filed: Mar. 2, 1978

[51] Int. Cl.³ .............................................. A61K 37/48
[52] U.S. Cl. ........................................................ 424/94
[58] Field of Search ........................................... 424/94

[56] References Cited
PUBLICATIONS

Sizer et al.; J. Pharm & Exp. Therap., vol. 84 pp. 363–373 (1945).
Sizer; Archives of Biochem., pp. 103–112 (1949).
Morpurgo et al.–Chem. Abst. vol. 80 (1974) p. 92, 629q.

Primary Examiner—Leonard Schenkman
Attorney, Agent, or Firm—Arnold, White & Durkee

[57] ABSTRACT

The enzyme p-Diphenol Oxidase, also known as laccase, is effective in the treatment and/or prevention of poison ivy dermatitis by topical application to one's skin before or after exposure to the poison ivy irritant, urushiol.

15 Claims, No Drawings

POISON IVY RELIEF COMPOSITION

BACKGROUND OF THE INVENTION

This invention relates to the treatment and/or prevention of dermatitis originating from the toxin urushiol which has been found to be present in poison ivy, poison oak, poison sumac, and the like.

A discussion and description of poison ivy dermatitis dates back to Chinese medical books of the seventh century. The first chemical experiments made in the United States on the toxin itself occurred over 100 years ago in 1858. The experimentor, Khittel, concluded that the poison was a volatile alkaloid, see Khittel, *Am. J. Pharm.*, 6(3), 542 (1858). It was not until the early 1930's that the carbon skelton of the irritant causing poison ivy dermatitis, known as urushiol, was defined by Hill and his students at Wesleyan University, see Hill, G., Matacotti, V., and Graham, W.; "The Toxic Principle of Poison Ivy", *J. Am. Chem. Soc.*, 56:2736, (1934). Urushiol was defined to be within the catechol group.

Poison ivy, poison oak, or poison sumac, upon contact with the skin causes severe inflamation, irritation, and blistering in certain individuals. Various enzymes and compounds have been proposed as a means of treating poison ivy dermatitis. Zirconium oxide is such a material; however, it has been frowned upon by the medical profession because of its allergic reactions in hypersensitive individuals. Additional agents such as potassium permanganate, hydrogen peroxide, and tyrosinase have been proposed; however, all have drawbacks either dealing with response time or toxicity. Applicants note Borris, U.S. Pat. No. 4,002,737, disclosing an enzyme catechol 1,2-oxygenase and catechol 2,3-oxygenase and mixtures thereof used in the detoxification of urushiol. Borris teaches that urushiol is detoxified by the enzyme catechol 1,2-oxygenase to an alkylated derivation cis, cismuconic acid. Catechol 2,3-oxygenase, which is also disclosed by Borris as a detoxifying agent of urushiol, results in a non-toxic alkylated derivative of alphahydroxy muconic semialdehyde when combined with urushiol. However, experiments have indicated that catechol 2,3-oxygenase is unstable in the presence of air. Its practical application as a drug in treating poison ivy dermatitis is questionable. See Boyer, P.D., *The Enzymes*, Vol. XII, p. 140, Academic Press, N.Y., N.Y. (1975). Borris discloses a mixed function oxidase reaction wherein the catechol is oxidized and the benzene ring structure is split within the reaction.

In addition to the Borris reference and articles disclosed therein, applicants note Sizer, I. W. and Prokesch, C. E.; "The Destruction by Tyrosinase of the Irritant Principles of Poison Ivy and Related Toxicants", *J. Pharm. & Exper. Therap.*, 84:363, (1945). Tyrosinase is known in the art as a detoxifying agent of urushiol. Tyrosinase attacks both mono- and polyphenols in a mono-function oxidase reaction. The enzyme, active primarily against ortho-diphenols, oxidizes the o-diphenol resulting in an unstable di-ketone which eventually breaks down and polymerizes. Tyrosinase is an endo-enzyme. It does not normally react in an aerobic environment but, rather, requires a closed cell reaction in a protective buffer environment. Because of this characteristic, the response time to treatment may be prolonged.

DESCRIPTION OF THE TABLES

Table 1 illustrates the results of the controlled toxin reaction test to determine the optimum concentration of the toxin to use in the prevention and treatment tests.

Table 2 illustrates the results of preventing a dermatitis by applying ferric ammonium citrate, ferric ammonium tartrate, tyrosinase or laccase to the skin before the urushiol toxin is applied.

Table 3 illustrates the results of treating or preventing a dermatitis by applying either of seven test compounds or laccase to the skin after the urushiol toxin is applied.

SUMMARY OF THE INVENTION

It is an object of this invention to provide materials for the treatment of dermatitis resulting from skin contact with poison ivy, poison oak, poison sumac, or the like.

It is another object of this invention to provide a method of treating dermatitis resulting from skin contact with poison ivy, poison oak, poison sumac, or the like.

It is yet another object of this invention to provide materials in preventing dermatitis resulting from skin contact with poison ivy, poison oak, poison sumac, or the like by topical application to the skin after contact with the toxin.

It is still another object of this invention to provide a method of preventing dermatitis resulting from skin contact with poison ivy, poison oak, poison sumac, or the like by topical application to the skin after contact with the toxin.

It is yet still another object of this invention to provide materials useful in preventing poison ivy dermatitis by topical application to the skin before contact with poison ivy, poison oak, poison sumac, or the like.

It is a further object of this invention to provide a method of preventing poison ivy dermatitis by topical application to the skin before contact with poison ivy, poison oak, poison sumac, or the like.

The invention embodies the application of the enzyme laccase (p-Diphenol Oxidase) to the skin for preventing and/or treating dermatitis resulting from contact with poison ivy, poison oak, poison sumac, or the like. While laccase is effective in both preventing and treating a dermatitis, Applicants have also discovered the use of an aqueous solution of ferric ammonium citrate or ferric ammonium tartrate in treating a dermatitis resulting from exposure to the irritant urushiol. The use of ferric ammonium citrate and ferric ammonium tartrate is the subject matter of U.S. patent application Ser. No. 882,900, filed Mar. 2, 1978, by Applicants.

DESCRIPTION OF THE INVENTION

It has been discovered that the enzyme laccase derived from the fungus *Polyporus versicolor* is effective in the treatment and/or prevention of poison ivy dermatitis. The principal toxin resulting in poison ivy dermatitis is urushiol. Applicants noted the use of the enzyme laccase in the treatment of poison ivy dermatitis since the same enzyme that degrades catechol might also degrade urushiol. Urushiol is a member of the catechol group. In accordance with this invention, application of the enzyme laccase derived from the fungus *Polyporus versicolor* to the skin area exposed or suspected of possible exposure to the irritant urushiol can ameliorate, eliminate, or prevent the dermatitis. The invention may be applied in aqueous or non-aqueous form with equal effectiveness. The preferred range if 0.01–1% by weight of laccase.

It is well-known in the art that the poison ivy plant itself, which is abundant with the toxin urushiol, is also a good source of laccase. It appears that such a condition may be essential for the plant to maintain proper protein balance. Applicants further noted that since laccase was actively present in the poison ivy plant, the presence of such an enzyme might account for the plant's survival due to the presence of urushiol. The disclosed enzyme laccase (p-Diphenol Oxidase) was isolated from a fungus *Polyporus versicolor* which is also known as *trametes*. However, laccase may also be found in the tree species *Rhus succedenea* and *R. vernicifera*. On the other hand, the Borris enzyme, discussed above, is not derived from a fungus but rather from the bacteria *Pseudomonas avilla* grown with benzoate as the sole carbon source. See, "Studies on Pyrocatechase", *J. of Bio. Chem.*, Vol. 242, No. 14, pp. 3270–3278.

The detoxification of the urushiol by laccase is represented by the following reaction:

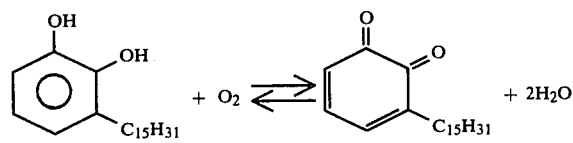

This reaction is a mono-function oxidase which results in an unstable di-ketone that eventually polymerizes. The enzyme laccase acts as a catalyst which oxidizes the ortho-diphenol to a harmless ortho-quinone. Unlike the mixed-function oxidase reaction of catechol 1,2-oxygenase and catechol 2,3-oxygenase in which both oxidation and destruction of the benzene ring occur within the single function, the mono-function oxidase reaction merely oxidizes the ortho-diphenol resulting in a quinone. Eventually the unstable di-ketone polymerizes but not within the defined mono-function oxidase reaction.

Unlike tyrosinase, laccase is an exo-enzyme. It is very stable in an aerobic condition and, in nature, acts in such an environment. This is significant for manufacturing purposes because the enzyme may be produced easily in large quantities and in a pure state. In addition, laccase's stability in open air is a particularly important factor in any dermatological preparation. As noted above, tyrosinase is an endo-enzyme which does not normally react in air but rather in a closed cell within a buffer hence, complicating its preparation within a suitable dermatological carrier for medicinal application to the skin in a convenient manner. Applicants, however, tested tyrosinase on the test subjects. The results are discussed below.

The enzyme laccase is classified under the commission number EC 1.10.3.2. An exact description of the enzyme's chemical composition can be found under the enzyme commission number in Bahrman, T. E., *Enzyme Handbook*, Vol. 1, Springer-Verlag, New York, N.Y., (1969).

In the embodiment of this invention directed to the treatment of poison ivy dermatitis resulting from skin contact with poison ivy, poison oak, poison sumac, or the like, the enzyme laccase may be applied directly to the skin thereby retarding and rapidly neutralizing the effect of the toxin. By this embodiment, there is available a method of treating poison ivy dermatitis resulting from contact with poison ivy, poison oak, poison sumac, or the like.

Alternatively, the enzyme laccase may be applied directly to the skin before contacting the toxin or after contacting the toxin yet before a dermatitis has developed as a preventive measure. If, after hiking through woods or similar out-door activity, one fears he may have contacted poison ivy, poison oak, poison sumac, or the like, he may apply the enzyme laccase directly to the affected skin area to prevent a dermatitis which would otherwise result. Such a topical application has been found effective in the prevention of poison ivy dermatitis.

The enzyme may be used in a pure state in the prevention and/or treatment of poison ivy dermatitis; however, excessive exposure to laccase may result in a dermatitis to the enzyme itself. Therefore, the most common practice would be to transport the enzyme within any suitable dermatological carrier. Applicants note that, unlike the disclosure of ferric ammonium citrate and ferric ammonium tartrate mentioned above, the enzyme laccase may be dissolved in solution or carried in a solid state within an inert cream or powder. Any carrier that would not inhibit the ability of the enzyme to act as a catalyst in the oxidation of the diphenol to a harmless quinone would be satisfactory. Suitable media may include cream-like, liquid-like, or solid-like carriers or combinations thereof. For example, finely divided inert powder such as talc or silica applied in dust form can suffice. Alternatively a non-reactive cream as polyethylene glycol may be used. An aqueous solution such as a phosphate buffer is also a possible medium. An oil-in-water emulsion may be preferred due to its improved resistance over a water based solution to body oils and perspiration. Several methods of applying the enzyme within a carrier are available. If a solution is used, it may be applied by hand or sprayed on in aerosol or pumped form. The solution may be stored on a disposable substrate such as a towelette or thin cotton pad. To apply the medication the pad or towelette would be swabbed onto the affected skin area. The above are merely examples of the possible class of acceptable dermatological carriers and are not intended to be exhaustive of all possible combinations which may be developed by one skilled in the art.

To further evaluate the treatment and/or prevention of a dermatitis following skin contact with the toxin, applicant's tested a combination treatment of ferric ammonium citrate or ferric ammonium tartrate in aqueous solution as discussed in our copending application covered with a cream-like or similar non-aqueous carrier containing laccase. As ferric ammonium citrate or ferric ammonium tartrate in solution form dried on the skin, the non-aqueous carrier containing laccase was applied to protect the ferric solution from body oils and perspiration. With this combination, one has both ferric ammonium citrate or ferric ammonium tartrate and laccase oxidizing the diphenol to a harmless di-ketone which eventually polymerizes. Applicants note, however, that such a combination did not appreciably improve the results that each treatment would provide independently.

The percent by weight of laccase within a solution or powder form does not appear to be a significant factor. Enough laccase must be present to neutralize the toxin in the treatment and/or prevention of the dermatitis. A miimum of 0.01% by weight laccase appears reasonable from the test results of applicants. Over several percent by weight of laccase may result in a dermatitis from the enzyme itself and solubility problems begin to arise at this concentration. The preferred range is 0.01–1% by weight of laccase within an acceptable dermatological carrier as discussed above.

In order to isolate the enzyme laccase from *Polyporus versicolor*, a sample of the fungus was obtained from a dead red oak tree in Iredell County, N.C. The fungus was first cultured on a solid agar containing 1% malt extract. A small fungal colony was transferred aseptically from the agar to a liquid nutrient medium prepared according to the formula by Fahraeus, G. as discussed in *Physiol. Plant.*, 7:704 (1954). The nutrient medium comprising 2 % by weight glucose, 0.27% sodium acetate, 0.2% ammonium chloride, 0.5% potassium di-hydrogen phosphate, 0.5% magnesium sulfate, 0.001% calcium chloride, 0.001% ferrous sulfate, 0.0001% manganese sulfate, 0.0001% zinc sulfate, 0.00001% copper sulfate, 0.000005% thiamine, .2% yeast extract, and distilled water sufficient to yield one liter of medium, was sterilized within a heat annealed glass bottle before transferring the fungus to it. The bottle was aerated with water-washed air which was passed through a drying tube full of glass wool to remove other contamination from the air line. The Polyporus was introduced into the nutrient medium and monitored at room temperature (23° C.) in light for four days under a vigorous aerating condition.

The enzyme laccase was then separated from the fungus suspended within the nutrient medium via Mosbach's method disclosed at length in Mosback, R. "Purification and Some Properties of Laccase from Polyporus Versicolor" in *Biochem. Biophys. Acta,* 73; 204–212 (1963). The method comprises introducing 2,5-xylidine into the aerated growth bottle. The fungus cells will begin to produce laccase upon the presence of 2,5-xylidine attempting to break the xylidine down. Xylidine is very similar to a catechol. For this reason the fungus cells produce laccase attempting to oxidize what they believe is a catechol. After two to three days at room temperature, the nutrient medium is filtered through a Buchner funnel removing the mycelia. The vacuum of the Buchner funnel withdraws the enzyme from the mycelia and filters it along with the nutrient medium. The medium is then saturated with ammonium sulfate which precipitates the enzyme. The gelatinous precipitate which forms floats at the top of the nutrient medium rather than sinking. The enzyme laccase is captured within this floating gelatinous precipitate which is skimmed off the surface and dialyzed to remove the ammonium and sulfate ions, leaving laccase. During the dialysis, the enzyme remaining in the dialysis bag is immersed in a dilute buffer of 0.02 M sodium phosphate (pH 6.0) for twelve hours to maintain a constant pH around the enzyme and to allow the migration of any traces of the ammonium or sulfate ions into the buffer. To store the enzyme laccase at the completion of the twelve hour bath, the dialysis bag is removed from the sodium phosphate buffer, its contents placed on a petri dish and frozen by dry ice at −60° C. A high vaccum is then placed on the frozen matter for approximately eight hours. The frozen liquid was sublimed leaving pure laccase in a powder form. The enzyme was then stored in vials and frozen until time for the experiment.

The experiments were conducted on two subjects exhibiting allergic reactions to urushiol. The toxin was isolated from fresh leaves and green stems of *Rhus toxicodendron*. The fresh plant material was covered in 400 ml. of ethanol and allowed to stand for four days at 5° C. The ethanol was then decanted and evaporated in a vacuum to yield a dark syrupy residue. The residue was subsequently partitioned between 50 ml. of benzene and 20 ml. of a 5% sodium chloride solution and allowed to evaporate in a vacuum. The result was a dark green oil. This oil was then chromatographed on a silica gel column and eluted by benzene. All parts showing a positive phenol test with 2% ethanolic ferric chloride were combined. The benzene was then evaporated in a vacuum to yield 0.2 grams of urushiol. See Corbett, M. D., and Billets, S., "Characterization of Poison Oak Urushiol", *J. Pharm. Sci.*, Vol. 64, No. 10, p. 1,715, 1,718 (October, 1975).

In the initial phase of the experiment an optimum control strength of the toxin urushiol for each subject was determined. Applicants wished to use a strong enough dilution to yield clear and distinct results yet not unduly harmful to the subjects. Six concentrations of the toxin diluted in ethanol ranging from 1:1000 to 1:100,000,000 by weight were tested. The toxin was applied with a five microliter capillary tube dispenser. To evaluate the results an arbitrary scale of zero to eight was developed. "0" indicates no reaction at all. "1" indicates that only tiny areas were affected with no edema and very slight erythema. "2" signifies very splotchy areas with no edema and slight erythema. "3" indicates splotchy areas with some erythema and slight edema. "4" indicates that the splotchy area had diverged into an area approximately two centimeters in diameter with erythema and edema. "5" indicates that the affected splotchy area had increased to 3 centimeters in diameter with continued erythema and edema. "6" signifies severe erythema and edema with a splotchy area of 3.5 centimeters in diameter and blisters beginning to form. "7" indicates that the splotchy area exhibited severe blistering, severe erythema, and severe edema. "8" signifies the maximum reaction with very severe erythema, very severe edema, and extremely severe blistering in a draining state with the affected area increasing to approximately 4 centimeters in diameter. The reactions to each concentration: were recorded on the zero to eight scale at six hours intervals through 48 hours and then at 72 and 96 hours. The results of the control test are illustrated in Table 1.

TABLE 1

| Concentration of Urushiol | Hours | | | | | | | | | |
|---|---|---|---|---|---|---|---|---|---|---|
| Solution | 6 | 12 | 18 | 24 | 30 | 36 | 42 | 48 | 72 | 96 |
| 1:100,000,000 | 0 | 0 | 0 | 0 | 0 | 0 | 0 | 0 | 0 | 0 |
| 1:10,000,000 | 0 | 0 | 0 | 0 | 0 | 0 | 0 | 0 | 0 | 0 |
| 1:1,000,000 | 0 | 0 | 0 | 0 | 0 | 0 | 0 | 0 | 0 | 0 |
| 1:100,000 | 0 | 0 | 0 | 0 | 0 | 1 | 2 | 3 | 3+ | 3+ |
| 1:10,000 | 0 | 0 | 2 | 4 | 5 | 5+ | 6 | 6 | 6 | 6 |
| 1:1,000 | 0 | 2 | 3 | 4 | 6 | 7 | 7+ | 8 | 8 | 8 |

The three most diluted solutions: 1:1,000,000; 1:10,000,000; and 1:100,000,000 did not cause a positive reaction (above zero) throughout the entire 96 hour test period. The 1:100,000 dilution did not produce a reaction until 36 hours and then only reached a maximum rating of three at 96 hours. The 1:10,000 concentration produced a reaction above zero at 18 hours indicating slight erythema within a very small splotchy area. The reaction gradually increased to a maximum rating of six at 42 hours and held such a reading for the remainder of the test. The most concentrated toxin solution resulted in a reading of two at 12 hours. Once again this reaction gradually increased until a maximum reading of eight was recorded at 48 hours. The results of this control test indicated that the 1:1,000 dilution may be too strong and may potentially harm the subjects over the extended period of tests; therefore, the 1:10,000 urushiol/ethanol solution was selected for both subjects as the control strength.

The second phase of the experiment was the principal phase. This phase was divided into two broad categories: prevention and treatment. Prevention as defined for this experiment means the application of the enzyme laccase and various other test compounds to the skin area before five microliters of the 1:10,000 urushiol/ethanol solution was applied. The treatment category consisted of the opposite procedure. The subject was first exposed to five micro-liters of the 1:10,000 urushiol/ethanol concentration and then treated with the enzyme laccase and various other test compounds.

Within each category of prevention and treatment, laccase suspended in a non-aqueous polyethlyene glycol carrier and laccase at 0.1% by weight in an aqueous phosphate buffer solution were tested. In order to evaluate the affect of time on each subject, laccase was applied before or after the toxin at specified time intervals. In the prevention category, laccase was applied immediately before, one hour before, two hours before, and six hours before the 1:10,000 urushiol/ethanol solution was applied. Each time period was a separate test. The same test parameters were repeated using the laccase carried in the phosphate buffer. In the treatment category, laccase was applied immediately after, one hour after, two hours after, and six hours after the urushol toxin. Once again each time period was a separate test. The same test parameters were repeated in the treatment category using 0.1% laccase by weight within the aqueous phosphate buffer. Therefore, within each category, prevention or treatment, a total of eight tests are run: four tests using laccase suspended in polyethylene glycol at the specified time intervals discussed above and four tests using laccase within a phosphate buffer base also at the specified time intervals. The results were recorded using the same zero to eight scale defined above at 24, 48, 72, 96, and 120 hours.

Within the prevention category, applicants tested ferric ammonium citrate, ferric ammonium tartrate, tyrosinase and laccase as a means of preventing poison ivy dermatitis before contact with poison ivy, poison oak, poison sumac, or the like. The ferric compounds are the subject of the copending application indentified above. The data on these ferric compounds is set forth for purposes of comparisons and illustration. Ferric ammonium citrate was tested at 2% and 20% by weight of ferric ammonium citrate in water. In addition, 20% and 30% ferric ammonium citrate by weight in an oil-in-water of the vanishing cream type sold under the trademark Velvachol were tested. The cream sold under the trademark Velvachol is a hydrophilic emulsion-type ointment base manufactured by the Texas Pharmacal Company, P.O. Box 1659, San Antonio, Tex. 78296.

Laccase was tried in non-aqueous form carried within polyethylene glycol and in aqueous form suspended in a phosphate buffer. The 2% ferric ammonium citrate illustrated little effectiveness in preventing a dermatitis when applied before contact with the toxin. The length of time between the application of 2% ferric ammonium citrate and the 1:10,000 urushiol/ethanol solution was irrelevant. 20% ferric ammonium citrate in water, on the other hand, improved the results obtained over the 2% ferric ammonium citrate. However, maximum reactions of six indicating severe erythema and edema still continued at 120 hours when applied one, two and six hours before contact with the toxin. Even when applied immediately before contact with the toxin, erythema and edema was still observed at 72 hours. Improvements in the results, however, were obtained with 20% ferric ammonium citrate in Velvachol. If applied immediately before contact with the toxin, there was very slight erythema and no edema observed. However,, if the 20% ferric ammonium citrate in Velvachol was applied over two hours before contact with the toxin, some erythema and slight edema was recorded at 120 hours. The results of the 30% ferric ammonium citrate in Velvachol were similar to the results of 20% ferric ammonium citrate in Velvachol. Therefore, the only time ferric ammonium citrate would appear to be of value in preventing a dermatitis is if applied immediately before contact with the toxin. Such a requirement is of limited practical value. One would rarely be in a position to constantly apply medication to his legs while walking through the woods.

20% and 30% by weight ferric ammonium tartrate in water have inconclusive results as to the prevention category. The results, recorded through only 72 hours, do not appear to correlate with respect to time. Ironically, preventive treatment six hours before exposure yielded the best results. Prevention of the dermatitis did not improve with the application of the compoound nearer the time of exposure to the toxin. Therefore, ferric ammonium tartrate appears to be of limited practical valve in preventing a poison ivy dermatitis.

Tyrosinase was tested in an aqueous phosphate buffer at a concentration of 0.83 mg/ml. While the length of time between the application of tyrosinase and the urushiol toxin did not appear to have a bearing on the results, the results indicated splotchy areas with no edema and slight erythema after 48 hours and some erythema and slight edema after 72 hours. Tyrosinase was less effective in preventing a dermatitis than 20% ferric ammonium citrate in Velvachol which appears of limited practical value. While the results are an improvement over the control test (Table 1), they indicate that tyrosinase was less effective as a medicinal application in preventing poison ivy dermatitis than 20% or 30% ferric ammonium citrate in Velvachol or laccase.

The enzyme laccase exhibited superior qualities in preventing a dermatitis when applied before contact with the 1:10,000 urushiol/ethanol solution. As shown in Table 2, virtually no reaction was observed following contact with the toxin.

TABLE 2

| | | Hours | | | | |
|---|---|---|---|---|---|---|
| Brief Description of Compounds Tested | | 24 | 48 | 72 | 96 | 120 |
| Concentrations by Weight | | | | | | |
| 2% | Ferric Ammonium Citrate in water | | | | | |
| | immediately before | 2 | 3 | 4 | 4 | 5 |
| | 1 hour before | 2 | 3 | 4 | 4 | 5 |
| | 2 hours before | 2 | 3 | 5 | 5 | 5 |

TABLE 2-continued

| Brief Description of Compounds Tested | Hours | | | | |
|---|---|---|---|---|---|
| | 24 | 48 | 72 | 96 | 120 |
| 6 hours before | 2 | 3 | 5 | 5 | 5 |
| 20% Ferric Ammonium Citrate in water | | | | | |
| immediately before | 1 | 3 | 4 | 4 | 5 |
| 1 hour before | 1 | 4 | 5 | 5 | 6 |
| 2 hours before | 2 | 4 | 6 | 6 | 6 |
| 6 hours before | 2 | 4 | 6 | 6 | 6 |
| 20% Ferric Ammonium Citrate in velvachol | | | | | |
| immediately before | 0 | 1 | 1 | 1 | 1 |
| 1 hour before | 0 | 1 | 1 | 2 | 3 |
| 2 hours before | 0 | 1 | 2 | 3 | 3 |
| 6 hours before | 0 | 2 | 2 | 3 | 4 |
| 30% Ferric Ammonium Citrate in velvachol | | | | | |
| immediately before | 1 | 1 | 1 | 1 | 1 |
| 1 hour before | 1 | 1 | 1 | 2 | 2 |
| 2 hours before | 1 | 2 | 2 | 2 | 3 |
| 6 hours before | 1 | 2 | 2 | 3 | 3 |
| 20% Ferric Ammonium Tartrate in water | | | | | |
| immediately before | 2 | 2 | 3 | | |
| 1 hour before | 4 | 5 | 5 | | |
| 2 hours before | 1 | 1 | 2 | | |
| 6 hours before | 0 | 0 | 1 | | |
| 30% Ferric Ammonium Tartrate in water | | | | | |
| immediately before | 2 | 2 | 3 | | |
| 1 hour before | 1 | 3 | 5 | | |
| 2 hours before | 2 | 3 | 5 | | |
| 6 hours before | 0 | 0 | 1 | | |
| Laccase in phosphate buffer (Aqueous) | | | | | |
| immediately before | 0 | 0 | 0 | 0 | 0 |
| 1 hour before | 0 | 0 | 0 | 0 | 1 |
| 2 hours before | 0 | 0 | 1 | 1 | 2 |
| 6 hours before | 0 | 1 | 2 | 2 | 2 |
| Laccase in polyethylene glycol (Non-Aqueous) | | | | | |
| immediately before | 0 | 0 | 0 | 0 | 0 |
| 1 hour before | 0 | 0 | 0 | 0 | 0 |
| 2 hours before | 0 | 0 | 1 | 1 | 1 |
| 6 hours before | 0 | 0 | 1 | 1 | 2 |
| Tyrosinase in phosphate buffer (Aqueous) | | | | | |
| immediately before | 1-2 | 1-2 | 4 | 4 | |
| 1 hour before | 1-2 | 1-2 | 4 | 4 | |
| 2 hours before | 1-2 | 1-2 | 4 | 4 | |
| 6 hours before | 1-2 | 1-2 | 4 | 4 | |

When laccase suspended within the aqueous solution was applied two hours before contact with the toxin a positive reaction was not observed until 72 hours, and then, it was only very slight erythema with no edema. Even after 120 hours only a slight erythema was recorded. When applied six hours before contact with the toxin, the maximum reaction was only a slight erythema. The results improve when the laccase within the non-aqueous polyethylene glycol is applied. No positive allergic reactions were ever observed when the enzyme was applied immediate before or one hour before contact with the poison ivy toxin. Even when applied two or six hours before contact with the toxin, the maximum positive reaction was a slight erythema with no edema.

The treatment category consisted of evaluating several compounds and one enzyme. As discussed above, each compound and enzyme under review was applied at four specified time intervals each being a separate test. The results are shown in Table 3.

TABLE 3

| Brief Description of Compounds Tested | Hours 24 | 48 | 72 | 96 | 120 |
|---|---|---|---|---|---|
| Concentrations by Weight | | | | | |
| 2% Ferric Ammonium Citrate in water | | | | | |
| immediately after | 2 | 3 | 5 | 5 | 5 |
| 1 hour after | 2 | 3 | 5 | 5 | 5 |
| 2 hours after | 2 | 4 | 6 | 6 | 6 |
| 6 hours after | 2 | 4 | 6 | 6 | 6 |
| 20% Ferric Ammonium Citrate in water | | | | | |
| immediately after | 0 | 0 | 1 | 1 | 1 |
| 1 hour after | 0 | 0 | 1 | 1 | 1 |
| 2 hours after | 0 | 1 | 1 | 1 | 2 |
| 6 hours after | 0 | 1 | 1 | 2 | 2 |
| 30% Ferric Ammonium Citrate in water | | | | | |
| immediately after | 0 | 0 | 0 | 0 | 0 |
| 1 hour after | 0 | 0 | 0 | 0 | 0 |
| 2 hours after | 0 | 0 | 0 | 1 | 1 |
| 6 hours after | 0 | 0 | 0 | 1 | 1 |
| 20% Ferric Ammonium Citrate in velvachol | | | | | |

TABLE 3-continued

| Brief Description of Compounds Tested | Hours | | | | |
|---|---|---|---|---|---|
| | 24 | 48 | 72 | 96 | 120 |
| immediately after | 0 | 0 | 1 | 1 | 1 |
| 1 hours after | 0 | 1 | 1 | 2 | 3 |
| 2 hours after | 0 | 1 | 2 | 2 | 3 |
| 6 hours after | 0 | 2 | 2 | 2 | 3 |
| 30% Ferric Ammonium Citrate in velvachol | | | | | |
| immediately after | 0 | 0 | 0 | 0 | 0 |
| 1 hour after | 0 | 0 | 1 | 1 | 1 |
| 2 hours after | 0 | 1 | 1 | 2 | 2 |
| 6 hours after | 0 | 1 | 2 | 2 | 2 |
| 20% Ferric Ammonium Sulfate in water | | | | | |
| immediately after | 0 | 0 | 0 | 0 | 0 |
| 1 hour after | 0 | 1 | 2 | 2 | 3 |
| 2 hours after | 0 | 1 | 2 | 3 | 3 |
| 6 hours after | 1 | 2 | 4 | 5 | 6 |
| 20% Ammonium Citrate in water | | | | | |
| immediately after | 1 | 4 | 4 | 5 | 5 |
| 1 hour after | 1 | 4 | 4 | 5 | 5 |
| 2 hous after | 1 | 4 | 4 | 5 | 5 |
| 6 hours after | 2 | 4 | 4 | 5 | 5 |
| 20% Ferrous Ammonium Sulfate in water | | | | | |
| immediately after | 1 | 2 | 2 | 3 | 4 |
| 1 hours after | 1 | 3 | 3 | 4 | 4 |
| 2 hours after | 1 | 3 | 4 | 4 | 4 |
| 6 hours after | 1 | 4 | 5 | 5 | 5 |
| 20% Ferric Sodium Ethylenediaminetetra-acetic (EDTA) Acid in water | | | | | |
| immediately ater | 2 | 4 | 5 | 5 | 5 |
| 1 hour after | 2 | 4 | 5 | 5 | 5 |
| 2 hours after | 2 | 4 | 5 | 5 | 5 |
| 6 hours after | 2 | 4 | 5 | 5 | 5 |
| 20% Ferric Ammonium Tartrate in water | | | | | |
| immediately after | 1 | 2 | 3 | | |
| 1 hours after | 1 | 1 | 1 | | |
| 2 hours after | 1 | 2 | 3 | | |
| 6 hours after | 0 | 1 | 2 | | |
| 30% Ferric Ammonium Tartrate in water | | | | | |
| immediately after | 0 | 1 | 2 | | |
| 1 hour after | 0 | 1 | 2 | | |
| 2 hours after | 0 | 1 | 2 | | |
| 6 hours after | 0 | 1 | 2 | | |
| Laccase in phosphate buffer (Aqueous) | | | | | |
| immediately ater | 0 | 0 | 0 | 0 | 0 |
| 1 hour after | 0 | 0 | 0 | 0 | 0 |
| 2 hours after | 0 | 0 | 0 | 1 | 1 |
| 6 hours after | 0 | 0 | 0 | 1 | 1 |
| Laccase in polyethylene glycol (Non-Aqueous) | | | | | |
| immediately afer | 0 | 0 | 0 | 0 | 0 |
| 1 hour after | 0 | 0 | 0 | 0 | 0 |
| 2 hours after | 0 | 0 | 0 | 1 | 1 |
| 6 hours after | 0 | 0 | 0 | 1 | 1 |
| Tyrosinase in phosphate buffer (Aqueous) | | | | | |
| immediately after | 1-2 | 1-2 | 5 | 5 | |
| 1 hour after | 2+ | 1-2 | 5 | 5 | |
| 2 hours after | 1 | 2 | 5 | 5 | |
| 6 hours after | 1-2 | 4 | 5 | 5 | |

Again, 2% ferric ammonium citrate by weight in water indicated relatively poor results. The dermatitis was reduced by approximately one point on the scale after 72 hours as compared to the control test (Table 1) when applied immediately after and one hour after the 1:10,000 urushiol/ethanol solution was applied. Additional results recorded with the 2% ferric ammonium citrate when applied two and six hours after the toxin indicated a slight improvement at 24 and 48 hours but no improvement at 72 and 96 hours.

20% by weight ferric ammonium citrate in water illustrated a marked improvement over the 2% ferric ammonium citrate. A maximum reading of one indicating no edema with very slight erythema was recorded at 120 hours for the first two tests wherein ferric ammonium citrate was applied immediately after and one hour after the toxin. As noted above with respect to the control test, without such a treatment severe erythema with edema would have resulted. The two and six hour tests of 20% ferric ammonium citrate in water illustrated a maximum positive reaction of two indicating a slight erythema with no edema whereas severe erythema with edema was noted on the control test at 42 hours.

30% by weight ferric ammonium citrate in water illustrated the most significant improvement over the control test. As seen in Table 3, a positive reading was never recorded on the first two tests when the treating compound was applied immediately after or one hour after the toxin. A maximum reading of one indicating no edema with very slight erythema was recorded for the third and fourth test when the treating compound was applied two and six hours after the toxin.

Applicants also tested 20% and 30% by weight ferric ammonium citrate in Velvachol. The treatment was not as effective as 20% and 30% ferric ammonium citrate in water. As shown in Table 3, the reactions tended to run one point higher on the scale than the water based test compound. In addition, a positive reading showing very slight erythema with no edema (rating of one on the scale) was noted at several points where initially no reaction was recorded with the same percent ferric ammonium citrate in water. Regardless, the results of the 20% and 30% by weight ferric ammonium citrate in Velvachol are still a significant improvement over the control test as shown in Table 1.

20% and 30% by weight ferric ammonium tartrate in water were also evaluated as a treating compound. Applicants decided to try ferric ammonium tartrate since it has been replaced by ferric ammonium citrate in the treatment of iron deficiency anemia. Applicants concluded, therefore, there may be a correlation between ferric ammonium citrate and ferric ammonium tartrate even in the treatment of poison ivy dermatitis. The results as shown in Table 3 indicate a definite improvement over the control test with respect to 20% ferric ammonium tartrate, a maximum reaction of three indicating some erythema with slight edema was observed at 72 hours. A reaction of six was noted on the 1:10,000 urushiol/ethanol control test at 72 hours. When applied one hour after application of the toxin, the maximum reaction was only a very slight erythema with no edema. While the results tended to worsen on the "two hour after" test, they improved on the "six hour after" test. Once again, the response to treatment by 20% ferric ammonium tartrate does not appear to be a linear relationship with time. Yet, the final results are an improvement over the control test up to 72 hours.

30% by weight ferric ammonium tartrate in water illustrated an improvement over the results of the 20% by weight ferric ammonium tartrate. The reactions for each test were identical at the designated time recording intervals. The time of application did not appear to be a factor. The results were a definite improvement over the control test up to 72 hours. The maximum reaction observed was a slight erythema with no edema at 72 hours. At this same time interval, the control test indicated severe erythema and severe edema. Therefore, ferric ammonium tartrate appears effective in treating a poison ivy dermatitis. However, ferric ammonium tartrate was not as effective as ferric ammonium citrate.

Tyrosinase was also tested as a treating compound. As shown in table 3, the results were very poor. Erythema with edema was observed in all test cases regardless of the length of time between application of the urushiol toxin and the treating compound. From applicant's experiments, tyrosinase was much less effective as a treating compound than ferric ammonium citrate or ferric ammonium tartrate.

The remaining compounds: 20% by weight ammonium citrate in water, 20% by weight ferric ammonium sulfate in water, 20% by weight ferrous ammonium sulfate in water, and 20% by weight ferric sodium ethylenediaminetetraacetic acid (EDTA) in water illustrated moderate to poor result in neutralizing the 1:10,000 urushiol/ethanol solution and retarding the appearance of a dermatitis. A maximum reading of five was recorded on at least one of the four tests run in each case. Ferric ammonium sulfate exhibited excellent qualities as a treating compound when applied immediately after contact with the toxin. However, the compound showed a marked decline in its ability to neutralize the toxin when applied two or six hours after the toxin. Ferric ammonium sulfate was the best of the four while ferric ammonium EDTA exhibited little effectiveness in neutralize the toxin. The use of ferric ammonium citrate and ferric ammonium tartrate as an effective method in the treatment of dermatitis resulting from contact with poison ivy, poison oak, poison sumac, or the like is the subject matter of a subject matter of a separate patent application by applicants.

Laccase suspended in a non-aqueous medium or carried within an aqueous solution such as a phosphate buffer exhibited excellent results in treating a dermititis resulting from contact with the toxin urushiol as shown in Table 3. Identical reactions were observed when either subject was treated with the laccase in an aqueous or non-aqueous form. A positive reaction was never observed when the enzyme was applied immediately after and one hour after the toxin. A maximum positive reaction was not recorded until 96 hours after the topical application of the toxin on the two and six hour tests. Even then, the maximum positive allergic reaction was a very slight erythema with no edema.

Final results clearly indicate that the use of the enzyme laccase derived from the fungus *Polyporus versicolor* whether suspended in a non-aqueous or aqueous medium is effective in the prevention and/or treatment of dermatitis resulting from contact between the skin and poison ivy, poison oak, poison sumac, or the like.

Further modifications and alternative embodiments of the invention may be apparent to those skilled in the art in view of this description. Accordingly, this description is to be construed as illustrative only and is for the purpose of teaching those skilled in the art the manner of carrying out the invention. It is to be understood that the forms of the invention herewith shown and described are to be taken as the presently preferred embodiment. As evident to one skilled in the art, various substitutions can be made to the foregoing disclosure without departing from the spirit of the invention.

What is claimed is:

1. A method for preventing dermatitis resulting from skin contact with urushiol toxin which comprises applying to the affected skin area an effective amount of the enzyme laccase derived from the fungus *Polyporus versicolor*.

2. A method according to claim 1, wherein the laccase is applied at a concentration of from about 0.01 to about 1.0 percent within an acceptable dermatological cream, solid or emulsion as a carrier.

3. A method of preventing poison ivy dermatitis wherein said method comprises applying to the affected skin area an effective amount of the enzyme laccase derived from the fungus *Polyporus versicolor*.

4. A composition useful in the prevention or treatment of dermatitis resulting from contact with a urushiol toxin comprising:
   between about 0.01 percent and about 1.0 percent by weight of the enzyme laccase derived from the fungus Polyporus versicolor; and
   the remaining weight being an acceptable dermatological cream, solid or emulsion as a carrier.

5. A method for treating dermatitis resulting from skin contact with a urushiol toxin which comprises applying to the affected skin area an effective amount of the enzyme laccase derived from the fungus *Polyporus versicolor*.

6. A method according to claim 1, wherein the application of the laccase to the skin takes place within six hours of said contact.

7. A method according to claim 1, wherein the application of the laccase to the skin takes place within one hour of said contact.

8. A method according to claim 2, wherein the application of laccase to the skin takes place within six hours of said contact.

9. A method according to claim 5, wherein the laccase is applied at a concentration of from about 0.01 to about 1.0 percent within an acceptable dermatological cream, solid or emulsion as a carrier.

10. A method for treating poison ivy dermatitis wherein said said method comprises applying to the effected skin area an effective amount of the enzyme laccase derived from the fungus *Polyporus versicolor*.

11. A composition according to claim 4, wherein the carrier an acceptable dermatological cream, solid or emulsion as a carrier.

12. A composition according to claim 4, wherein the dermatological carrier is a suitable cream.

13. A composition according to claim 4, wherein the dermatological carrier is a suitable solid.

14. The composition according to claim 4, wherein the dermatological carrier is a suitable powder.

15. A composition according to claim 4, wherein the dermatological carrier is a suitable emulsion.

* * * * *

UNITED STATES PATENT AND TRADEMARK OFFICE
CERTIFICATE OF CORRECTION

PATENT NO. : 4,259,318
DATED : March 31, 1981
INVENTOR(S) : Nanda V. Duhe and Donald L. Hendrix It is certified that error appears in the above—identified patent and that said Letters Patent is hereby corrected as shown below:

Column 1, line 15, change ", see" to --. See--;
　　　　　line 17, change "skelton" to --skeleton--;
　　　　　line 19, change ", see" to --. See--;
　　　　　line 39, change "derivation" to --derivative-- and change "cis, cismuconic" to --cis,cis-muconic-- with --cis,cis-- being in italics;
　　　　　line 42, change "alphahydroxy" to --alpha-hydroxy-- with --alpha-- being in italics;
　　　　　line 62, change the "o" of "o-diphenol" to be in italics;
Column 2, line 24, change "in" to --for--;
Column 2, line 42 and
Column 3, line 11, change "p-Diphenol Oxidase" to --p-diphenol oxidase--;
Column 2, line 58, change "resulting in" to --producing--.
Column 3, line 13, change "trametes" to --Trametes--.
Column 4, line 30, after "Alternatively" add --,-- and after "cream" add --such--;
　　　　　line 67, change "miimum" to --minimum--.
Column 5, line 31, change "Mosback" to --Mosbach--;
　　　　　line 33, change "73;" to --$\underline{73}$;--.

UNITED STATES PATENT AND TRADEMARK OFFICE
CERTIFICATE OF CORRECTION

PATENT NO. : 4,259,318

DATED : March 31, 1981

INVENTOR(S) : Nanda V. Duhe and Donald L. Hendrix

It is certified that error appears in the above—identified patent and that said Letters Patent is hereby corrected as shown below:

Column 7, line 21, change "polyethlyene" to --polyethylene--;
line 34, change "shol" to --shiol--;
line 56, after "water" add --emulsion--.
Column 8, line 19, change ",," to --,--;
line 38, change "compoound" to --compound--;
line 41, change "valve" to --value--.
Column 11, Table 3, lines 30, 45 and 51, change "ater" to --after--.
Column 14, line 51 and
Column 15, line 13, after "solid" add --, buffered solution--;
Column 14, line 61, "Polyporus versicolor" should be in italics.
Column 16, line 4, after "carrier" add --is--.

Signed and Sealed this

Eleventh Day of May 1982

[SEAL]

Attest:

*Attesting Officer*

GERALD J. MOSSINGHOFF

*Commissioner of Patents and Trademarks*